US00PP30419P3

(12) United States Plant Patent
Randag

(10) Patent No.: US PP30,419 P3
(45) Date of Patent: Apr. 16, 2019

(54) CALLA LILY PLANT NAMED 'SUNSET PASSION'

(50) Latin Name: *Zantedeschia sprengeri*
Varietal Denomination: Sunset Passion

(71) Applicant: Dümmen Group B.V., De Lier (NL)

(72) Inventor: Cecilius Jan-Jochem Randag, 't Zand (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,644

(22) Filed: Dec. 7, 2017

(65) Prior Publication Data

US 2018/0177110 P1 Jun. 21, 2018

Related U.S. Application Data

(60) Provisional application No. 62/498,157, filed on Dec. 15, 2016.

(51) Int. Cl.
*A01H 5/02* (2018.01)

(52) U.S. Cl.
USPC ..... Plt./490
CPC ..... *A01H 5/02* (2013.01)

(58) Field of Classification Search
USPC ..... Plt./490
See application file for complete search history.

*Primary Examiner* — Annette H Para
(74) *Attorney, Agent, or Firm* — The Webb Law Firm

(57) ABSTRACT

'Sunset Passion' is a new variety of calla lily plant having inflorescences with a red/orange-colored spathe that produces 4-15 inflorescences per tuber. The height of the top of an inflorescence above the soil can reach up to 49 cm. The leaves are green with transparent maculations present and have a leathery texture.

1 Drawing Sheet

Botanical classification: *Zantedeschia sprengeri*.
Varietal denomination: 'Sunset Passion'.

BACKGROUND OF THE NEW PLANT

The present invention comprises a new and distinct cultivar of calla lily, botanically known as *Zantedeschia sprengeri* and hereinafter referred to by the cultivar name 'Sunset Passion'.

'Sunset Passion' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* selection referred to as Z050779 (female parent, unpatented) with a *Zantedeschia sprengeri* selection referred to as Z030458 (male parent, unpatented). 'Sunset Passion' was selected in 2011 by the inventor in 't Zand, The Netherlands as one flowering plant within the progeny of the stated cross.

The first act of asexual reproduction of 'Sunset Passion' by tissue culture was performed by the inventor in September of 2011 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown from 12-14 weeks in 14 cm pots in 't Zand, The Netherlands under greenhouse conditions, which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Sunset Passion' which, in combination, distinguish this calla lily as a new and distinct cultivar:

1. Red/orange-colored spathes; and
2. Large inflorescences.

Further, when compared to calla lily plant named 'Orange County' (U.S. Plant Pat. No. 27,863), the upper surface spathe color of 'Orange County' varies between Orange Group RHS 25A and 25B, whereas the upper surface spathe color of 'Sunset Passion' varies between Yellow-Orange Group RHS 21A and 21B, with a secondary color that varies between Orange-Red Group RHS 34A and N34B.

Table 1 provides similarities and differences of 'Sunset Passion' to its parents, *Zantedeschia sprengeri* selection Z050779 and *Zantedeschia sprengeri* selection Z030458.

TABLE 1

| 'Sunset Passion' | Similarities | Differences |
|---|---|---|
| Z050779 | Spathe shape<br>Number of inflorescences | Spathe color<br>Spathe size<br>Plant height |
| Z030458 | Spathe size<br>Plant height | Spathe shape<br>Spathe color |

BRIEF DESCRIPTION OF THE DRAWING

The accompanying photographic drawing illustrates the new variety, with the colors being as nearly true as is possible with color illustrations of this type:

FIG. 1 is a photograph of multiple plants of the new variety.

DESCRIPTION OF THE NEW PLANT

The plant:

*Size*.—Height of the leaf canopy above the soil: 18-40 cm. Height of top of inflorescences above the soil: 26-49 cm. Diameter: 6-8.5 cm.

*Form*.—Erect.

*Number of inflorescences per tuber*.—Size 14-16 cm in diameter: 4-7 inflorescences. Size 16-18 cm in diameter: 7-8 inflorescences. Size 18-20 cm in diameter: 8-10 inflorescences. Size 20+ cm in diameter: 10-15 inflorescences.

*Branches*.—Average Number: 10.4. Color: Between Green Group RHS 143A and Yellow-Green Group RHS 144B.

*Leaves*.—Size: Width: 3-9.5 cm. Length: 10-24 cm. Number per plant: 13-20. Shape: Lanceolate. Apex: Apiculate. Base: Attentuate. Margin: Undulate; having a color between Green Group RHS 137A and Yellow-Green Group RHS 144A. Color: Upper surface: Green Group RHS 137A to Yellow-Green Group RHS 147B, having transparent maculations of approximately White Group RHS 155A. Lower surface: Yellow-Green Group RHS 144A to 146B, having transparent maculations of approximately White Group RHS 155A. Veins: Configuration: Pinnate. Color: Upper Surface: Green Group RHS 143A to Yellow-Green Group RHS 144B. Lower Surface: Green Group RHS 143A to Yellow-Green Group RHS 144A. Surface quality: Leathery. Petiole: Length: 8-20 cm. Diameter: 3-7 mm. Color: The base is White Group RHS 155A, the upper part is Yellow-Green Group RHS 144A to 146B.

*Roots*.—Color: White. Branching: Similar to other *Zantedeschia* varieties.

The inflorescence and seeds:

*Spathe*.—Size: Length (measured from opening to tip): 6.5-10 cm. Width: 4.5-6 cm. Height: 6-10 cm. Color: Upper surface: Varies between Yellow-Orange Group RHS 21A and 21B, with a secondary color that varies between Orange-Red Group RHS 34A and N34B. Lower surface: Yellow Group RHS 12A, with a secondary color that varies between Orange-Red Group RHS N34B and 35C. Vein color: Between Yellow-Green Group RHS 144A and Orange-Red Group N34B. Shape: Funnel. Apex: Apiculate. Base: Attenuate. Margin: Rounded to undulate. Texture: Smooth (upper and lower surfaces).

*Spadix*.—Size: Length: 27-52 mm. Diameter: 5-10 mm. Color: Between Yellow Group RHS 9B and Yellow-Orange Group RHS 17A. Position relative to spathe: Upright.

*Peduncle*.—Size: Length: 20-39 cm. Diameter: 5-8 mm. Color: The upper part is Yellow-Green Group RHS 144A, the lower part is Green-White Group RHS 157C. Texture: Smooth.

*Reproductive organs*.—Location of female organs: Basal position of the spadix. Location of male organs: Upper position of the spadix. Perianth: Conspicuous. Stamens: Presence: Not visible before pollen release. Number: More than 20. Pollen amount: Abundant; similar to 'Picasso' (U.S. Plant Pat. No. 15,282). Color: Between White Group RHS 155A and 155B. Anther: Shape: Round. Length: Less than 1 mm. Color: Between Yellow Group RHS 9B and Yellow-Orange Group RHS 17A. Filament: Length: Less than 1 mm. Color: Between White Group RHS 155A and 155B. Pistils: Number: 15 to 30. Length beyond perianth: About 1 mm. Stigma: Shape: Round. Size: Less than 1 mm. Style: Length: Less than 1 mm. Color: Varies between Yellow-Orange Group RHS 14A and 14B. Ovaries: Texture: Smooth. Length: Between 1 to 10 mm. Width: Between 1 to 10 mm. Color: Top color is between Green Group RHS 143B and Yellow-Green Group RHS 145D, the bottom color is between White Group RHS 155B to Green-White Group RHS 157C.

*Seeds*.—Length: 4-7 mm. Width: 3-6 mm. Color: Between Yellow-Green Group RHS 150A and 151A. Amount: Between 1-60.

General:

*Disease resistance*.—No unusual susceptibility to diseases noticed to date.

*Pest resistance*.—No unusual susceptibility to pests noticed to date.

*Heat tolerance*.—No heat tolerance.

*Hardiness*.—Not hardy.

*Flowering*.—In general, the time from planting to first flowering takes eight weeks. However, tubers stored for a longer period before planting may flower earlier — up to five weeks after planting.

*Lastingness*.—About two weeks on the plant.

*Fragrance*.—None.

I claim:

1. A new and distinct variety of calla lily plant named 'Sunset Passion' as herein described and illustrated.

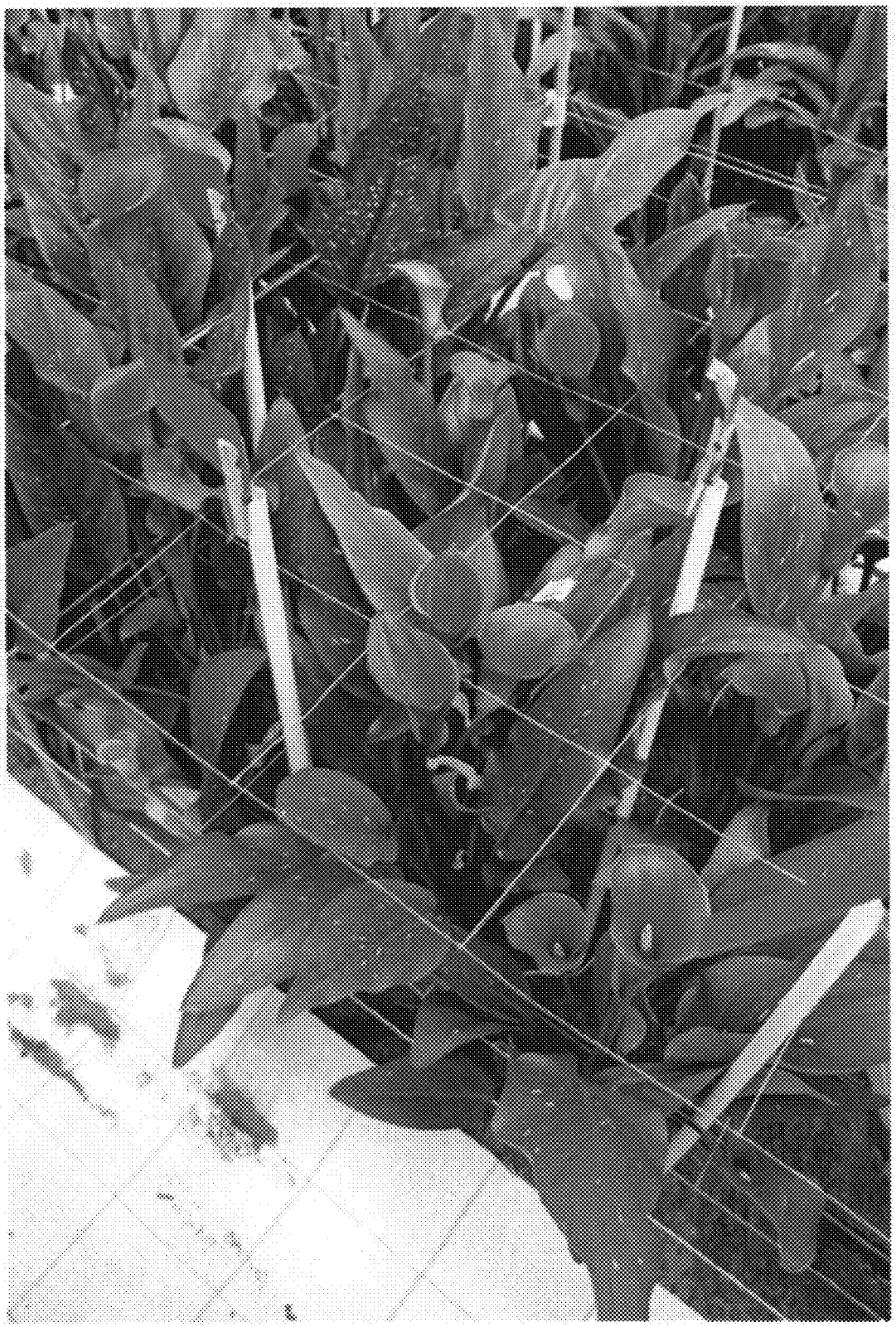

* * * * *